US 9,983,163 B2

(12) United States Patent
Hassibi et al.

(10) Patent No.: US 9,983,163 B2
(45) Date of Patent: May 29, 2018

(54) INTEGRATED ELECTRO-ANALYTICAL BIOSENSOR ARRAY

(71) Applicant: Board of Regents, The University of Texas System, Austin, TX (US)

(72) Inventors: Arjang Hassibi, Austin, TX (US); Arun Manickam, Sunnyvale, CA (US); Rituraj Singh, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1272 days.

(21) Appl. No.: 13/873,684

(22) Filed: Apr. 30, 2013

(65) Prior Publication Data
US 2014/0318958 A1 Oct. 30, 2014

(51) Int. Cl.
*G01N 27/327* (2006.01)
(52) U.S. Cl.
CPC .................. *G01N 27/3277* (2013.01)
(58) Field of Classification Search
CPC ............ G01N 27/327; G01N 27/3277; G01N 27/4145–27/4148; G01D 5/24; G01P 15/125; G01L 9/12
See application file for complete search history.

(56) References Cited

U.S. PATENT DOCUMENTS

| | | | |
|---|---|---|---|
| 7,399,585 B2 | 7/2008 | Gau | |
| 7,572,624 B2 | 8/2009 | Gumbrecht et al. | |
| 8,349,167 B2 | 1/2013 | Rothberg et al. | |

(Continued)

FOREIGN PATENT DOCUMENTS

| | | |
|---|---|---|
| EP | 1368498 A2 | 12/2003 |
| WO | 2009082706 A1 | 7/2009 |

OTHER PUBLICATIONS

Y. Temiz, et al., Robust Microelectrodes Developed for Improved Stability in Electrochemical Characterization of Biomolecular Layers, IEEE Sensors 2010 Conference, pp. 1051-1055 (2010).*

(Continued)

*Primary Examiner* — Maris R Kessel
(74) *Attorney, Agent, or Firm* — Robert A. Voigt, Jr.; Winstead, P.C.

(57) ABSTRACT

A biosensor pixel for measuring current that flows through the electrode surface in response to electrochemical interactions and a biosensor array architecture that includes such biosensor pixels. The biosensor pixel includes an electrode transducer configured to measure a current generated by electrochemical interactions occurring at a recognition layer placed directly on top of it in response to an electrical voltage placed across an electrode transducer-electrolyte interface. The biosensor pixel further includes a trans-impedance amplifier connected to the electrode transducer, where the trans-impedance amplifier is configured to convert the current into a voltage signal as the electrochemical interactions occur. Additionally, the biosensor pixel includes a 1-bit comparator coupled to the trans-impedance amplifier and a 1-bit digital-to-analog converter coupled to the 1-bit comparator, where the 1-bit digital-to-analog converter injects different levels of charge into an input of the trans-impedance amplifier at each cycle based on an output of the 1-bit comparator.

17 Claims, 16 Drawing Sheets

(56) References Cited

U.S. PATENT DOCUMENTS

| | | | |
|---|---|---|---|
| 2004/0038420 A1* | 2/2004 | Gelbart | G01N 27/3276 436/149 |
| 2005/0238123 A1* | 10/2005 | Ranganathan | G01D 5/24 375/343 |
| 2010/0052080 A1 | 3/2010 | Garcia Tello et al. | |
| 2010/0276734 A1 | 11/2010 | Josowicz et al. | |
| 2010/0300899 A1 | 12/2010 | Levine et al. | |
| 2012/0168306 A1 | 7/2012 | Hassibi et al. | |

OTHER PUBLICATIONS

R.R. Singh, et al., A Compact Parasitic-Insensitive Dual-Frequency ΔΣ Modulated CMOS Capacitive Architecture, IEEE, pp. 242-245 (2010).*

P.M. Levine et al., Active CMOS Array for Electrochemical Sensing of Biomolecules, IEEE 2007 Custom Intergrated Circuits Conference (CICC), pp. 826-828 (2007).*

A. Manickam, et al., A CMOS Electrochemical Impedance Spectroscopy (EIS) Biosensor Array IEEE Transactions on Biomedical Circuits and Systems, vol. 4, No. 6, pp. 379-380 (Dec. 2010).*

* cited by examiner

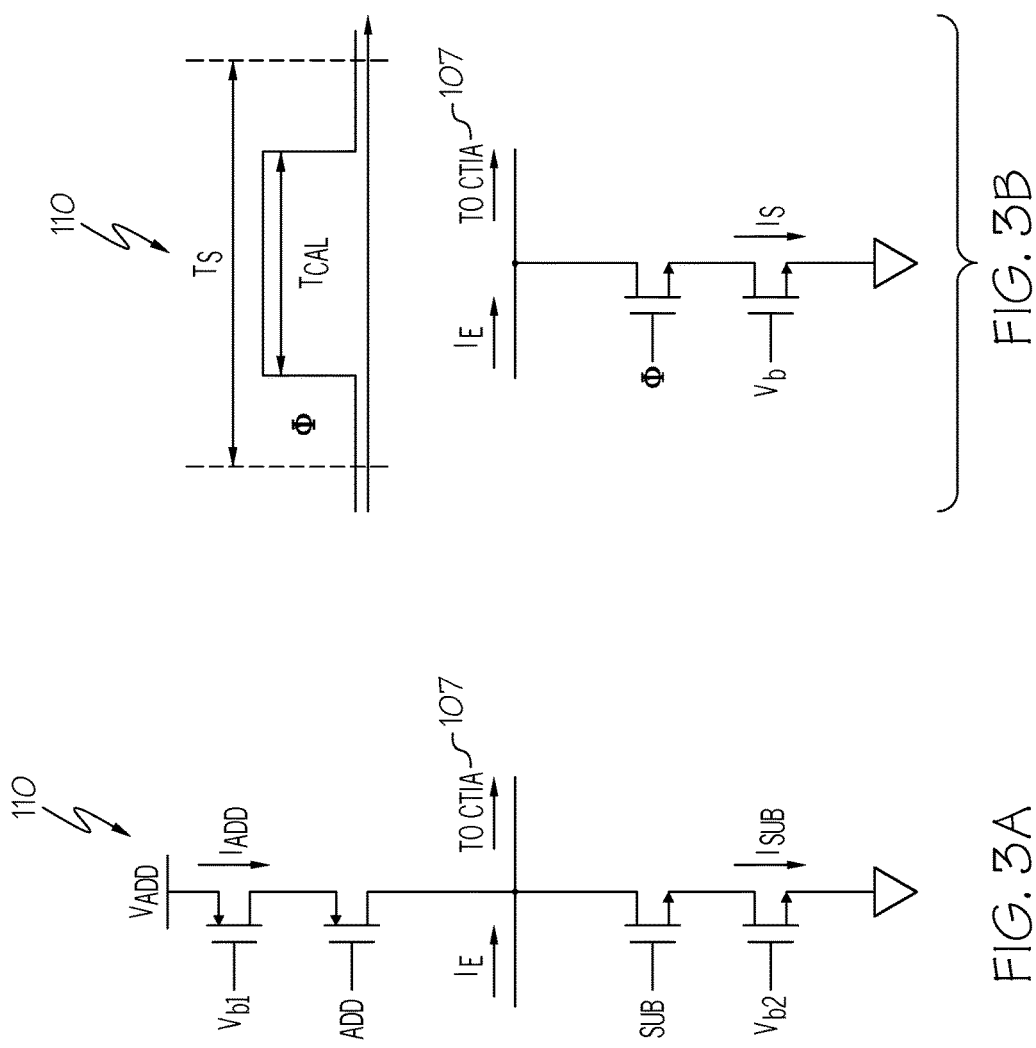

INTEGRATED ELECTRO-ANALYTICAL BIOSENSOR ARRAY

TECHNICAL FIELD

The present invention relates generally to biosensors and bioelectronics, and more particularly to a biosensor pixel configured to measure the current that flows through the electrode transducer surface in response to and/or instantiated by electrochemical or biochemical interactions and a semiconductor-integrated biosensor array architecture that includes a plurality of such biosensor pixels.

BACKGROUND

Biosensors are devices that use biochemical reactions to identify and detect various molecules and biochemical analytes. Biosensors are widely used in different life-science applications, ranging from environmental monitoring and basic life science research to Point-of-Care (PoC) in-vitro diagnostics. Biosensors are known to be very sensitive and also extremely versatile in terms of detection. They can efficiently detect a small number of almost any type of analyte molecule or molecular structure, once a proper recognition (capturing) molecule is identified. Example analytes that have been detected using biosensors include DNA and RNA strands, proteins, metabolites, toxins, micro-organisms, and even explosives molecules.

All biosensors, independent of the analyte they are trying to detect, include two key building blocks. One is the molecular recognition layer attached to a solid-phase surface which is responsible for identifying and/or interacting with and/or reacting with and/or capturing the specific target analyte from the sample. The other is the sensor apparatus which detects and/or quantifies the interactions of the recognition layer with the analytes and provides a measurable output, generally in the form of an electrical signal. The molecular recognition layer typically comprises of carefully engineered and surface-assembled molecules in addition to analyte-specific capturing molecules attached to a solid-phase surface. Examples of such include spotted or synthesized DNA oligonucleotides, aptamers, antigens or antibodies attached to solid surfaces such as glass slides, microbeads, electrodes, semiconductor materials, or dense polymers. Examples of a sensor apparatus include optical-, MEMS- and/or electronics-based transducers connected to a low-noise electronic circuit.

So far, there have been many detection methods that have been adopted in biosensor systems. A detection method is generally defined as the specific type of physiochemical mechanism designed into the molecular recognition layer, analytes, and the sample environment that make the capturing of the specific target analytes detectable. The most widely used detection methods are different types of optical (e.g., fluorescence, bioluminescence) and electro-analytical (e.g., potentiometric, amperometric, impedimetric). It is also customary to classify biosensors based on their detection method (e.g., in bioluminescence-based biosensors, the interaction of the analyte and probes results in a bioluminescence phenomenon which is detected by a specific sensor with a transducer sensitive to bioluminescence signals).

One general class of biosensors which is relevant to the present invention is electro-analytical. The operating principle of such biosensors is based on measuring changes in the current, voltage or impedance associated with biomolecular interactions taking place at a recognition layer at the interface of an electrode-electrolyte interface. In these systems, the electrode typically acts as the solid-phase on which the recognition layer is attached to the electrode. While electro-analytical methods are extremely versatile, they are more challenging to implement compared to their optical counterparts. The main reason is because of their transducer element (i.e., electrode-electrolyte structure) which requires to be placed in intimate proximity of the recognition layer and capturing probes to efficiently sense analytes. In addition, creating large scale biosensor arrays, which are imperative in biotechnology high-throughput screening applications, are very difficult, as electrically accessing individual electrodes within the array becomes the bottleneck.

BRIEF SUMMARY

In one embodiment of the present invention, a biosensor pixel comprises an electrode transducer with a recognition layer, where the electrode transducer is configured to measure a current generated by electrochemical interactions between an analyte and the recognition layer. The biosensor pixel further comprises a trans-impedance amplifier connected to the electrode transducer, where the trans-impedance amplifier is configured to convert the current into a voltage signal in real-time as the electrochemical interactions occur. Additionally, the biosensor pixel comprises a quantizer circuit coupled to the trans-impedance amplifier with a differential input, where the quantizer circuit is configured to convert a value of the voltage signal into a digital value. Furthermore, the biosensor pixel comprises a charge injection circuit coupled to the quantizer circuit, where the charge injection circuit is configured to place a controllable current or a net charge into an input of the trans-impedance amplifier. In addition, the biosensor pixel comprises an in-pixel feedback network coupled to the quantizer circuit, where the feedback network comprises the charge injection circuit and where the feedback network is configured to control an operation of the charge injection circuit based on values of the digital value.

In another embodiment of the present invention, a biosensor pixel comprises an electrode transducer with a recognition layer, where the electrode transducer is configured to measure a current generated by electrochemical interactions between an analyte and the recognition layer. The biosensor pixel further comprises a trans-impedance amplifier connected to the electrode transducer, where the trans-impedance amplifier is configured to convert the current into a voltage signal in real-time as the electrochemical interactions occur. Furthermore, the biosensor pixel comprises a controlled voltage source coupled to a positive input of the trans-impedance amplifier to set a potential of the electrode transducer to a value of the controlled voltage source. Additionally, the biosensor pixel comprises a 1-bit comparator coupled to the trans-impedance amplifier. In addition, the biosensor pixel comprises a 1-bit digital-to-analog converter coupled to the 1-bit comparator, where the 1-bit digital-to-analog converter injects different levels of charge into an input of the trans-impedance amplifier at each cycle based on an output of the 1-bit comparator.

In another embodiment of the present invention, a planar two-dimensional (2D) biosensor array architecture comprises a plurality of biosensor pixels assembled in rows and columns, where each of the plurality of biosensor pixels comprises an inert electrode transducer configured to sense a current generated by electrochemical interactions occurring at individual recognition layer regions of every pixel in response to different electrical voltages being placed across an electrode transducer-electrolyte interface for that pixel.

Furthermore, each of the plurality of pixels comprises a trans-impedance amplifier connected to the electrode transducer, where the trans-impedance amplifier is configured to convert the current into a voltage signal in real-time as the electrochemical interactions occur. Additionally, each of the plurality of pixels comprises a controlled voltage source coupled to a positive input of the trans-impedance amplifier. Furthermore, each of the plurality of pixels comprises a 1-bit comparator coupled to the trans-impedance amplifier. Additionally, each of the plurality of pixels comprises a 1-bit digital-to-analog converter coupled to the 1-bit comparator, where the 1-bit digital-to-analog converter injects different levels of charge into an input of the trans-impedance amplifier at each cycle based on an output of the 1-bit comparator. In addition, the biosensor array architecture comprises row and column decoders coupled to the plurality of pixels, wherein the row and column decoders are configured to select individual pixels of the plurality of pixels and access them one at a time.

The foregoing has outlined rather generally the features and technical advantages of one or more embodiments of the present invention in order that the detailed description of the present invention that follows may be better understood. Additional features and advantages of the present invention will be described hereinafter which may form the subject of the claims of the present invention.

BRIEF DESCRIPTION OF THE SEVERAL VIEWS OF THE DRAWINGS

A better understanding of the present invention can be obtained when the following detailed description is considered in conjunction with the following drawings, in which:

FIGS. 3A-3C illustrate examples of the charge injection circuit of the pixel in accordance with an embodiment of the present invention;

DETAILED DESCRIPTION

Figure 1:
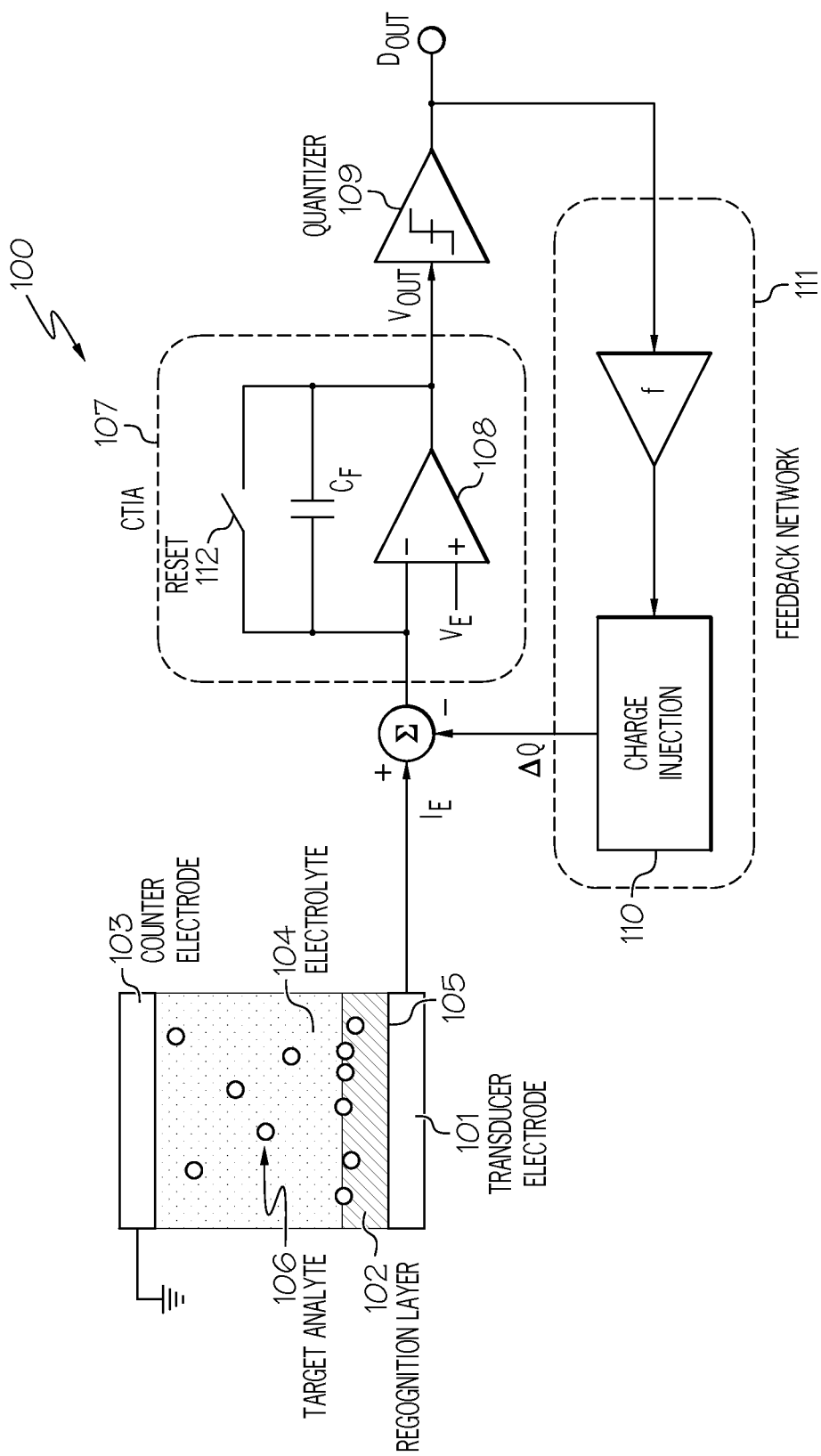
FIG. 1 illustrates the basic block diagram of a pixel in accordance with an embodiment of the present invention.

The principles of the preset invention relate to biosensors that use electro-analytical detection methods for detection and quantification of bio-molecules. There are two distinct components in the present invention that operate in concert to enable its functionality. One is the molecular recognition layer component that identifies specific bio-molecules and/or bio-molecular structures from an aqueous sample and the other is the electro-analytical sensor that translates such molecular identification events to a measurable output signal.

The present invention takes advantage of the recognition layer, attached to a solid-phase, to identify bio-molecules and/or bio-molecular structures that in the context of biosensors are generally referred to as "analytes." The design, implementation, and fabrication of such molecular recognitions layers that typically consist of specific capturing probes, such as DNA, RNA, or antibodies, attached to the solid-phase through linker molecules are widely known in the art. To translate molecular recognition and capturing events into a measurable signal, the present invention uses a current-based electro-analytical sensor that is built using electronic circuits that are integrated in a semiconductor substrate.

In typical electro-analytical biosensors, changes in the current, voltage or the impedance, associated with the bio-molecular interactions and reactions taking place are measured at an electrode-recognition layer interface which is in contact with the electrolyte. It is widely known in the art that such changes may occur when specific bio-molecule analytes, such as DNA, RNA, or peptides, herein referred to as the target molecules, interact with and/or are captured by the capturing probes of the recognition layer during the biosensing process. In certain cases, the target molecules can be chemically modified to include electro-active species, herein referred to as labels, to increase the changes in the detectable signals. In such cases, upon successful capturing, the labels generally get into the intimate proximity of the electrode and create unique electrochemical interactions and signals in response to an electrical voltage placed across the electrode-recognition layer interface. In most cases, the labels are a reduction-oxidation (redox) molecule that may or may not participate in a redox cycling process as a donor and/or an acceptor. Examples of such molecules include certain variants of organometallic compounds, such as Ferrocene (Fe$(C_5H_5)_2$), or certain aromatic compounds, such as Methylene Blue ($C_{16}H_{18}N_3SCl$). Other examples of labels are different redox enzymes, such as Glucose Oxidase or Horserdish Peroxide (HRP), which can create a highly electro-active molecule, such as Hydrogen Peroxide ($H_2O_2$) using specific substrate molecules.

In the present invention, independent of using a label or not, the current that flows through the electrode surface is specifically measured in real-time as an indicator of molecular interactions within the recognition layer. The target molecules captured at the recognition layer crate a unique current response when a specific electrical voltage is placed across the electrode-recognition layer interface. Such current signals during typical biosensing measurements are generally small (below 10 µA/mm² of electrode area and above 1 fA/mm²) and typically vary slowly (below 10 kHz bandwidth); however, in certain embodiments of the present invention, the current is measured at higher frequencies. Hence, the principles of the present invention also implement electronic circuits that enable high-performance current detection.

In embodiments of the present invention, the biosensor array is built using a complementary metal-oxide-semiconductor (CMOS) semiconductor substrate, in which the electro-analytical biosensor, including the current sensor circuitry built using the active devices (e.g., transistors and diodes) and passive devices (e.g., resistors, capacitors and inductors), are built using the CMOS process. Furthermore, the electrode transducers are also built using the metal layers of the CMOS back-end process.

In embodiments of the present invention the electro-analytical biosensor includes a molecular recognition layer immobilized and attached to the solid-phase surface of the electrode transducer integrated in a CMOS substrate. The capturing probe layer may include specific organic recognition molecules, such as DNA strands or peptides which are chemically modified to attach directly to the surface of the electrode or indirectly attach, through a linker molecule, to the surface of the electrode.

In the description herein, methods are discussed to build "integrated electro-analytical biosensor arrays," which take advantage of electronic integrated circuits (ICs) fabricated in a CMOS semiconductor substrate, as their sensing apparatus. In these systems, the biosensor array is created by placing recognition layers in intimate proximity of a CMOS-integrated electrode array that is connected to an integrated sensor circuitry embedded in the IC.

It is noted that biosensor arrays, including the systems described herein, are essentially a plurality of densely packed biosensors that can detect multiple target molecules in parallel from a sample in real-time. Individual sensors within the biosensor array are herein referred to as the "pixel." In the context of the present invention, these pixels consist of an electrode transducer that contains the recognition layer and the dedicated integrated circuitry that performs current sensing, signal quantization and signal enhancement and/or signal processing.

Electro-Analysis Pixel Architecture

The integrated electro-analytical biosensor array, discussed herein, consists of a plurality of independent pixels densely packed in a semiconductor substrate fabricated using processes, such as CMOS. The number of pixels is typically greater than 10 and less than $10^6$. Furthermore, individual pixels may have distinct addressable recognition layers consisting of a specific capturing probe. Referring now to FIG. 1, FIG. 1 illustrates the basic block diagram of the pixel 100 in accordance with an embodiment of the present invention. Pixel 100 includes:

I. An electrode transducer 101 with a recognition layer 102 and a counter electrode 103 in the solution (electrolyte) 104, which can sense the current that passes through its interface 105 that is generated by the electrochemical interactions between the analyte 106 and recognition layer 102 that is denoted by $I_E$;

II. A trans-impedance amplifier (TIA) 107, which converts $I_E$ into a voltage signal while maintaining the potential of the voltage to $V_E$. In certain embodiments of the present invention, a capacitance trans-impedance amplifier circuit (CTIA) is used, which converts an input current signal to a voltage by integrating the current onto its feedback capacitor, $C_F$, using an operational amplifier (op-amp 108);

III. A quantizer circuit 109, which converts the analog output voltage value of TIA (or CTIA) 107 into a discrete and digital value $D_{OUT}$;

IV. A charge injection circuit 110, which can insert or extract a controllable current or net charge ($\Delta Q$) into or out of the input of TIA (or CTIA) 107; and V. A feedback network 111 which controls the operation of the charge injection circuit in real-time based on the values of $D_{OUT}$.

Electrode Transducer 101 (FIG. 1)

Most ICs today are built using semiconductor very large scale integration (VLSI) micro-fabrication processes. The CMOS fabrication process is currently the "flagship" process of VLSI micro-fabrication processes and the majority of ICs (both analog and digital) are built using this particular technology. In a typical CMOS process, active devices (including MOS transistors) are fabricated in a planar silicon substrate on a wafer level; while interconnects (i.e., wirings) are built using aluminum (and occasionally copper) metal layers embedded in a thin dielectric layer on top of the silicon substrate. One advantage of CMOS processes for electro-analysis, besides the capability to integrate electronic circuit components, is that the metal layer can be used to create an electrode transducer. For example, this can be done by creating an opening in the passivation layer that covers the top metal layer of a standard CMOS process as shown in FIGS. 2A-2B.

Figure 2A:
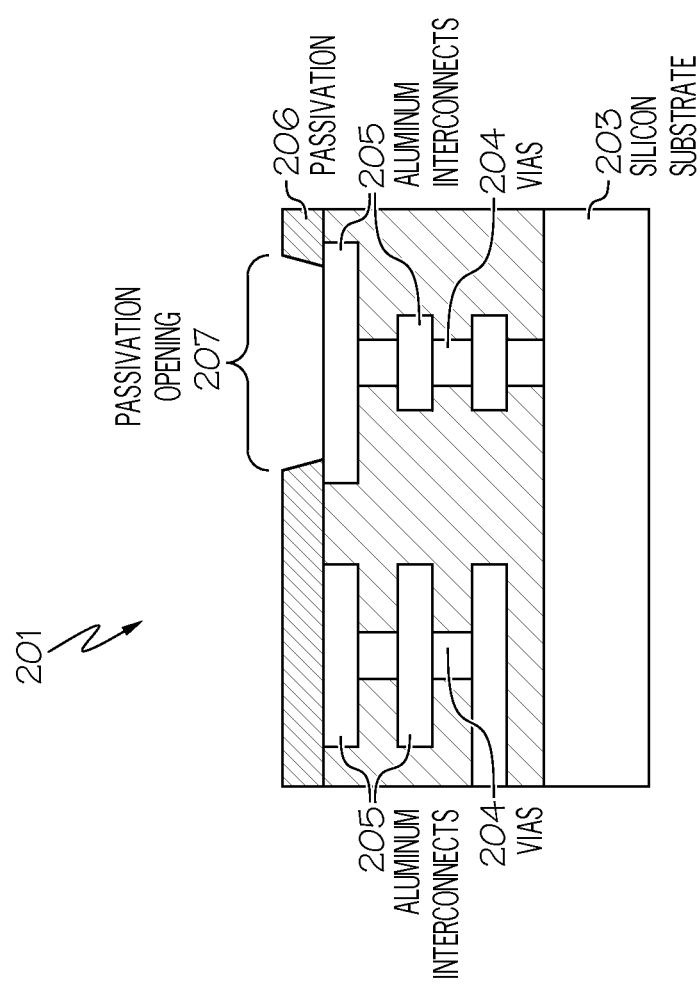
FIG. 2A illustrates the cross-sections of a standard CMOS integrated circuit in accordance with an embodiment of the present invention.
Figure 2B:
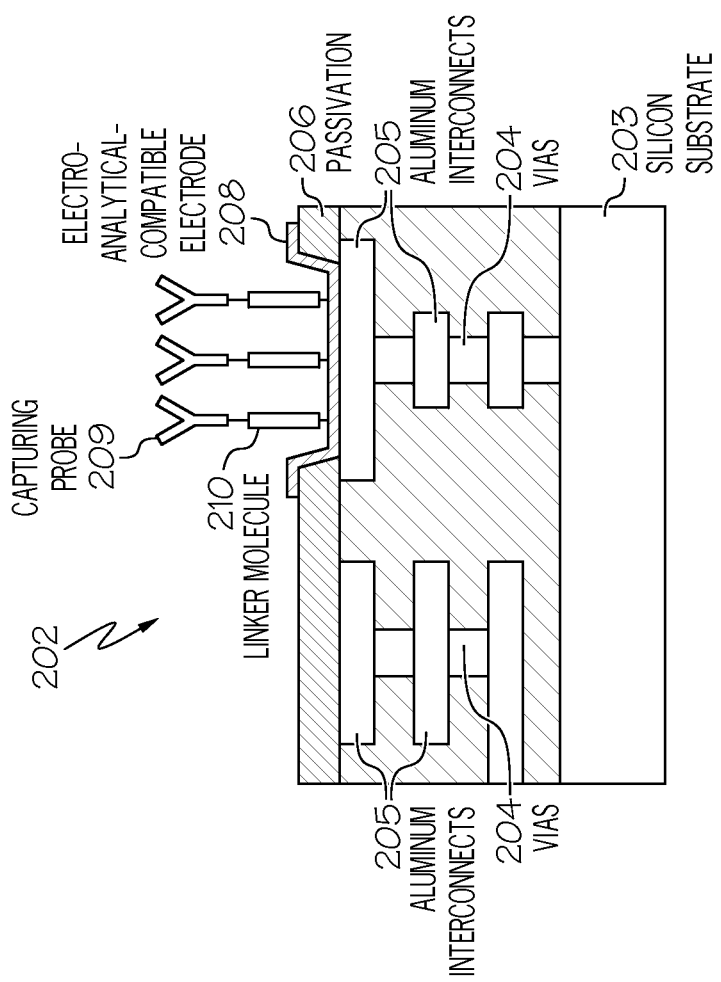
FIG. 2B illustrates a modified CMOS integrated circuit for electro-analytical biosensing in accordance with an embodiment of the present invention.

FIG. 2A illustrates the cross-sections of a standard CMOS integrated circuit 201 in accordance with an embodiment of the present invention and FIG. 2B illustrates a modified CMOS integrated circuit 202 for electro-analytical biosensing in accordance with an embodiment of the present invention. Referring to FIGS. 2A and 2B, CMOS integrated circuit 201 and modified CMOS integrated circuit 202 both include a silicon substrate 203, vias 204, aluminum interconnects 205 and a passivation layer 206. Such components are well known in the art and will not be discussed herein for the sake of brevity.

FIG. 2A further illustrates that while creating an opening 207 in the passivation layer that covers the top metal layer is a simple and straightforward approach, it is not the optimal solution for electro-analytical biosensing as aluminum is not considered to be an optimal metal for creating biosensing electrode transducers. This is mainly due to its susceptibility to corrosion when exposed to biological buffers that are effectively highly conductive electrolytes. To address this problem, as shown in FIG. 2B, one can deposit or grow layers of other materials on top of the aluminum surface and change it into a robust and bio- and electro-analytical-compatible electrode 208. Some example bio- and electro-analytical compatible materials that can be placed using various thin-film depositions methods on top of aluminum are noble metals, such as gold (Au) or platinum (Pt), or oxides, such as alumina, $SiO_2$, $TiO_2$ and $HfO_2$. The dimensions of such CMOS-integrated electrodes 202 can vary from 0.2 µm×0.2 µm to 100 µm×100 µm and the integrated biosensor array can have as low as 10 such electrodes to as many as $10^6$. Also, the electrodes may have different shapes (e.g., square, rectangular or circular).

It is deemed to be important to mention herein that the transducer electrode of the present invention is effectively identical to the working electrode that is used in conventional electro-analysis methods including amperometry, voltammetry, and impedance spectroscopy. Typically, a three-electrode setup is used in conventional electro-analysis, where a reference electrode and a counter electrode are required to be placed in the electrolyte in addition to the working electrode In the present invention, while the transducer electrode (i.e., working electrode) is incorporated in individual pixels, it is not necessary to include a dedicated counter or reference electrode in every pixel, as one can share the counter and the reference electrodes in the biosensor array systems without affecting the operation of pixels. In other words, a plurality of the biosensing pixels in the array may have a single reference and/or counter electrode. Such reference and counter electrodes may or may not be integrated in CMOS as the transducer electrode (working electrode) is created.

It is noted that there are many different methods to create recognition layers on top of the electrode. Such methods are widely known in the field of electrochemistry and electroanalysis. Referring to FIG. 2B, in the present invention, the electrode transducer includes a recognition layer that includes molecular capturing probes 209 immobilized and attached to the surface of electrode 208. Some example capturing probes 209 are single-strand DNA, RNA strands, aptamers, proteins, or antibodies which are chemically modified to attach directly to the solid-phase surface of electrode 208 or indirectly being immobilized, generally through a linker molecule 210, such as carbon chains, polymers, or sugars that are attached to the solid-phase surface of electrode 208.

Referring to FIGS. 1 and 2B in combination, it is noted that the current generated in electro-analytical biosensors, denoted by $I_E$, is bi-directional, meaning that the current can go into or come out of transducer electrode 101. The directionality of the $I_E$ depends on the applied potential to the electrode, $V_E$, the molecules involved in the signal transduction process, including capturing probe 209 and target analyte 106, and the label (if any). Typically, $V_E$ is a fixed DC potential and is established by means of a negative feedback of TIA 107. However, in preferred embodiments, $V_E$ can be a time-varying potential signal having a sine, square, saw-tooth waveform or a combination of the foregoing.

Capacitive Trans-Impedance Amplifier (CTIA) 107 (FIG. 1)

Referring to FIG. 1, CTIA 107 consists of opamp 108, negative feedback capacitor $C_F$, a reset switch 112 across $C_F$, and the voltage source $V_E$ which is connected to the positive terminal of operational amplifier 108 (see FIG. 1). In this system, if reset switch 112 is activated at t<0 and released at t=0, then the output of CTIA 107, denoted by $V_{OUT}$, at the end of measurement time, $T_S$, becomes $$V_{OUT}(T_S) = \frac{1}{C_f}\int_0^{T_S} I_E(t)\,dt + V_E \quad (EQ\ 1)$$

which for a constant $I_E$ during $T_S$, can be simplified to $$V_{OUT}(T_S) = \frac{I_E T_S}{C_f} + V_E \quad (EQ\ 2)$$

One important characteristic of CTIA 107 is that the voltage at its input, which is effectively the electrode transducer voltage, follows $V_E$. This is particularly useful when CTIA 107 is connected to electrode transducer 101 by ensuring that the voltage applied to the electrode is set to a controllable $V_E$ and hence voltage across the electrode-recognition layer 105 becomes tunable during the operation by simply changing $V_E$. As evident in (EQ 1) and (EQ 2), this has little effect on measuring $I_E$ since changing $V_E$ only adds a known offset to the measured $V_{OUT}$.

Quantizer Circuit 109 (FIG. 1)

Referring to FIG. 1, quantizer circuit 109 compares the output voltage at the end of the measurement time, $V_{OUT}(T_S)$, to a single or a plurality of reference voltages in order to convert the $V_{OUT}(T_S)$ into a digital signal represented by $D_{OUT}$. In the simplest case, quantizer 109 can be a 1-bit clocked (dynamic) comparator in which $V_{OUT}$ is compared to a fixed DC voltage, $V_C$, at t=$T_S$. In the more complicated case, quantizer 109 can be a multi-bit Analog-to-Digital Converter (ADC), which is widely known in the art.

Charge Injection Circuit 110 (FIG. 1)

Referring to FIG. 1, charge injection circuit 110 performs the task of injecting a controlled current or net charge into the input node of CTIA 107 during each measurement. There are multiple IC techniques to implement this functionality. Some examples are:

A controlled-amplitude and adjustable current, $I_{CAL}$, is directly added to or subtracted from the input of CTIA 107 (and integration onto $C_F$). In this case, if $I_{CAL}$ is remains unchanged during $T_S$, then the net added or subtracted charge, dented by $\Delta Q$, becomes equal to $I_{CAL} \times T_S$. FIG. 3A illustrates an example implementation of this where two current sources (top PMOS and bottom NMOS) can add $I_{CAL}=I_{ADD}$ or subtract $I_{CAL}=I_{SUB}$ by enabling ADD or SUB digital signals, respectively, in accordance with an embodiment of the present invention.

II. A fixed-amplitude current pulse, $I_S$, with a controllable width $T_{CAL}$ ($T_{CAL}<T_S$), is used to add or subtract $\Delta Q=I_S \times T_{CAL}$ from the input of CTIA 107. FIG. 3B illustrates an example implementation of this where clock $\Phi$ connects $I_{CAL}$ onto the input of CTIA 107 for $T_{CAL}$ second during $T_S$ in accordance with an embodiment of the present invention.

III. A capacitor $C_S$ is first charged to an adjustable reference voltages, $V_{CAL}$, and subsequently its stored charge $\Delta Q=C_S \times V_{CAL}$ is added or subtracted from the input of CTIA 107 (and hence $C_F$). FIG. 3C illustrates an example switch-level implementation of this where by toggling signal $\Phi$, $\Delta Q$ is injected into the input of CTIA 107 in accordance with an embodiment of the present invention.

Feedback Network 111 (FIG. 1)

Referring to FIG. 1, feedback network 111 effectively combines $D_{OUT}$ with charge injection circuit 110. The goal of this block is to determine and inject $\Delta Q$ within each measurement cycle based on $D_{OUT}$ of the previous cycles. Feedback network 111 in the context of the present invention is typically implemented using digital circuits, where $D_{OUT}$ is first applied to a digital filter and/or gain blocks comprised of logic gates, adders, shift registers, and multipliers, and subsequently, the result is used to control the functionality of charge injection circuits 110 previously discussed. In typical cases, the output of network 111 is a plurality of digital signals that controls the duration (e.g., $T_{CAL}$) and/or amplitude and/or frequency and/or directionality of injected charges.

Background Signal and Background Subtraction

Referring to FIG. 1, $I_E$ that passes through the electrode generally consist of two parts. One part is the current which is a function of the analyte specific interactions with recognition layer 102 and the other is the "background" signal which is independent of biosensing. The background current is generally considered to be non-informative and it is preferred to be subtracted from the signal prior to detection.

In embodiments of the present invention, this current is subtracted by using charge injection circuitry 110 at every cycle. In embodiments of the present invention, the subtracted charge is independent of $D_{OUT}$ and feedback network 111.

Embodiment of the Pixel

Figure 4:
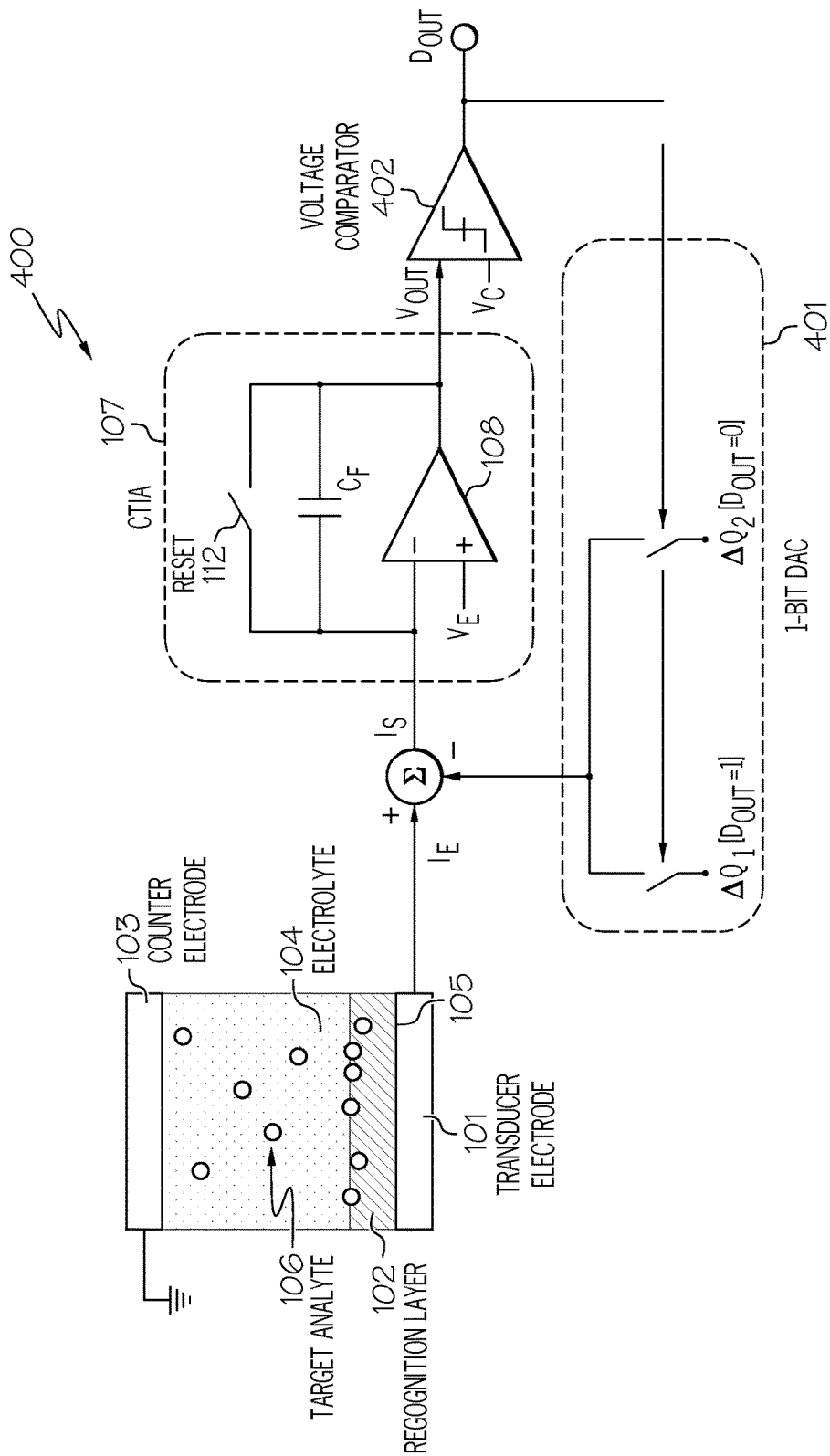
FIG. 4 illustrates an alternative embodiment of the present invention of a biosensor pixel.

FIG. 4 illustrates an alternative embodiment of the present invention of a biosensor pixel 400 in accordance with an embodiment of the present invention. Referring to FIG. 4, one pixel embodiment of the present invention is to implement a sigma-delta ($\Sigma$-$\Delta$) modulator to measure $I_E$ generated by electrochemical reactions at electrode transducer 101. This specific circuit architecture offers the advantage of noise shaping capabilities of $\Sigma$-$\Delta$ modulators, thereby improving the current measurement dynamic range. In this pixel architecture, the feedback network forms a Digital-to-Analog Converter (DAC) 401 which subtracts $\Delta Q$ that represents $D_{OUT}$ in each cycle (i.e., ever $T_S$ seconds), while CTIA 107 acts as the integrator of the $\Sigma$-$\Delta$ modulator as illustrated in the biosensor pixel 400 of FIG. 4.

In an example embodiment, a 1-bit quantizer 402 is used such that $D_{OUT}=0$ for $V_{OUT}(nT_S)<V_C$, and $D_{OUT}=1$ for $V_{OUT}(nT_S)>V_C$, where n is an integer number indicating the cycle number. Feedback network 401 then subtracts $\Delta Q_1$ and $\Delta Q_2$ ($\Delta Q_1>\Delta Q_2$) for $D_{OUT}=1$ and $D_{OUT}=0$, respectively, at the next cycle, as shown in the biosensor pixel 400 of FIG. 4. The $D_{OUT}$ sequence can then be digitally filtered and down-sampled using a decimation filter to estimate $I_E$.

In one embodiment, $D_{OUT}$ changes $T_{CAL}$, the width of the current pulse $I_S$ which is introduced at the input of CTIA 107. Hence, by making use of pulse width modulation (i.e., different pulse widths $T_{CAL}(1)$, $T_{CAL}(2)$ ... $T_{CAL}(N)$) for different quantized $D_{OUT}$ values $D_1, D_2 ... D_N$, it is possible to create the feedback DAC 401 and enable the $\Sigma$-$\Delta$ operation.

In another embodiment, the capacitor $C_F$ is charged to different reference voltages $V_{REF}(1)$, $V_{REF}(2)$, ..., and $V_{REF}(N)$, based on $D_{OUT}$ and its charge is then injected into the input of CTIA 107.

One advantage of the $\Sigma$-$\Delta$ modulator described herein is that it can also accommodate background current subtraction without requiring any additional circuitry. The approach to do this is to subtract a fixed charge that represents the background signal using DAC 401 and add the charge representing $D_{OUT}$ on top of that.

Figure 5:
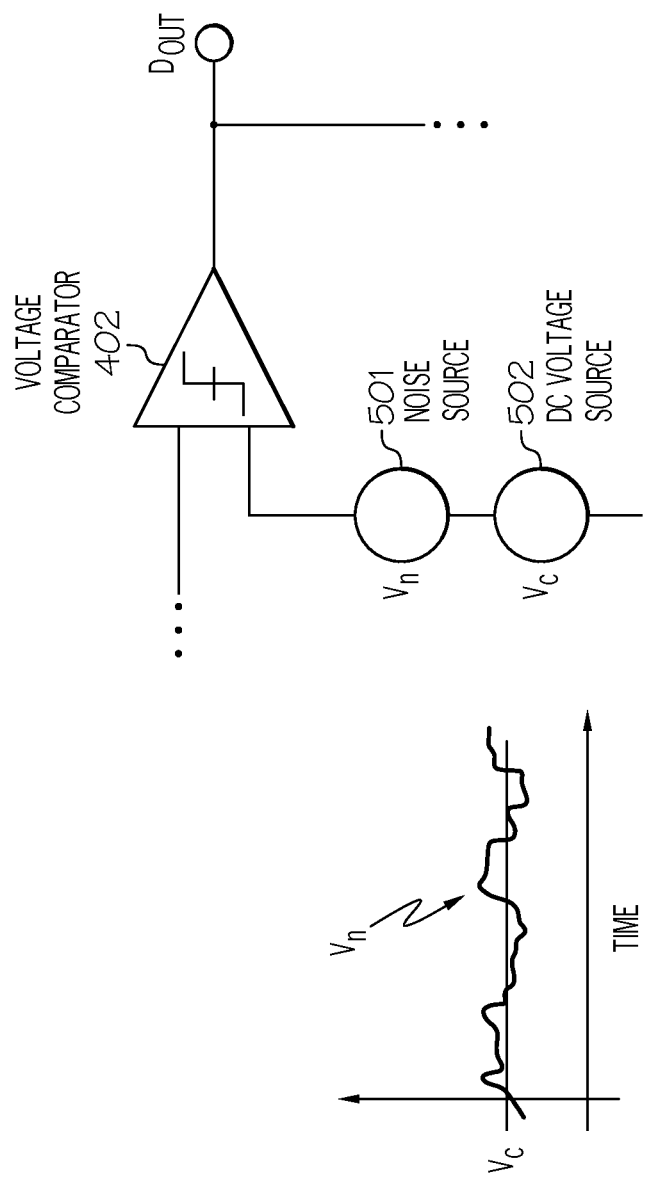
FIG. 5 illustrates removing the idle tones in accordance with an embodiment of the present invention.

It is important to note here that utilizing 1-bit quantizers offer lower complexity, when compared to multi-bit quantizers. However, 1-bit $\Sigma$-$\Delta$ modulators inherently suffer from idle tones, when the input is a DC signal. It is widely known in the art that these idle tones occur due to the deterministic nature of the quantization noise and generally appear as tones with frequencies proportional to the input DC amplitude applied. In the present invention, such a problem is solved by using noise dithering which is a widely implemented technique in the field. In one implementation of dithering, one can add a white noise source 501 to the DC voltage source 502 at the input of voltage comparator 402 (FIG. 4) as shown in FIG. 5 to randomize the quantization noise and remove the idle tones in accordance with an embodiment of the present invention.

In one embodiment of the present invention, pixel 100, 400 (FIGS. 1 and 4) is built using a CMOS fabrication process.

In one embodiment of the present invention, recognition layer 102 (FIGS. 1 and 4) and electrode-transducer 101 (FIGS. 1 and 4) is placed on top of the pixel circuitry.

In one embodiment of the present invention, capture probes 209 (FIG. 2B) within recognition layer 102 and/or target molecules 106 (FIGS. 1 and 4) are nucleic acid strands, such as DNA or RNA or aptamers.

In an alternative embodiment, capturing probes 209 within recognition layer 102 and/or target molecules 106 include amino acid chains (e.g., small peptides, proteins, antibodies).

In one embodiment, target molecules 106 are chemically modified to include electro-active labels to enhance the detectable signals. The labels may be a reduction-oxidation (redox) molecule that may or may not participate in a redox cycling process as a donor and/or an acceptor. Such molecules and structures are widely known in the art. Examples include certain variants of organometallic compounds, such as Ferrocene ($Fe(C_5H_5)_2$), or certain aromatic compounds, such as Methylene Blue ($C_{16}H_{18}N_3SCl$). Other examples of labels include redox different redox enzymes, such as Glucose Oxidase or Horserdish Peroxide (HRP), which can create a highly reactive molecule, such as Hydrogen Peroxide ($H_2O_2$) using specific substrate molecules.

In summary, referring to FIGS. 1, 4 and 5, one embodiment of the present invention for a pixel includes:

I. An electrode transducer 101 with recognition layer 102 connected to CTIA 107;

II. A CTIA circuit 107 with its positive input connected to the controlled voltage source;

III. A 1-bit comparator 402 with a noise dithered reference voltage 501; and IV. A 1-bit DAC 401 (based on $D_{OUT}$) which can inject different levels of charge into the input of CTIA 107 at each cycle.

Biosensor Array Architecture

Figure 6:
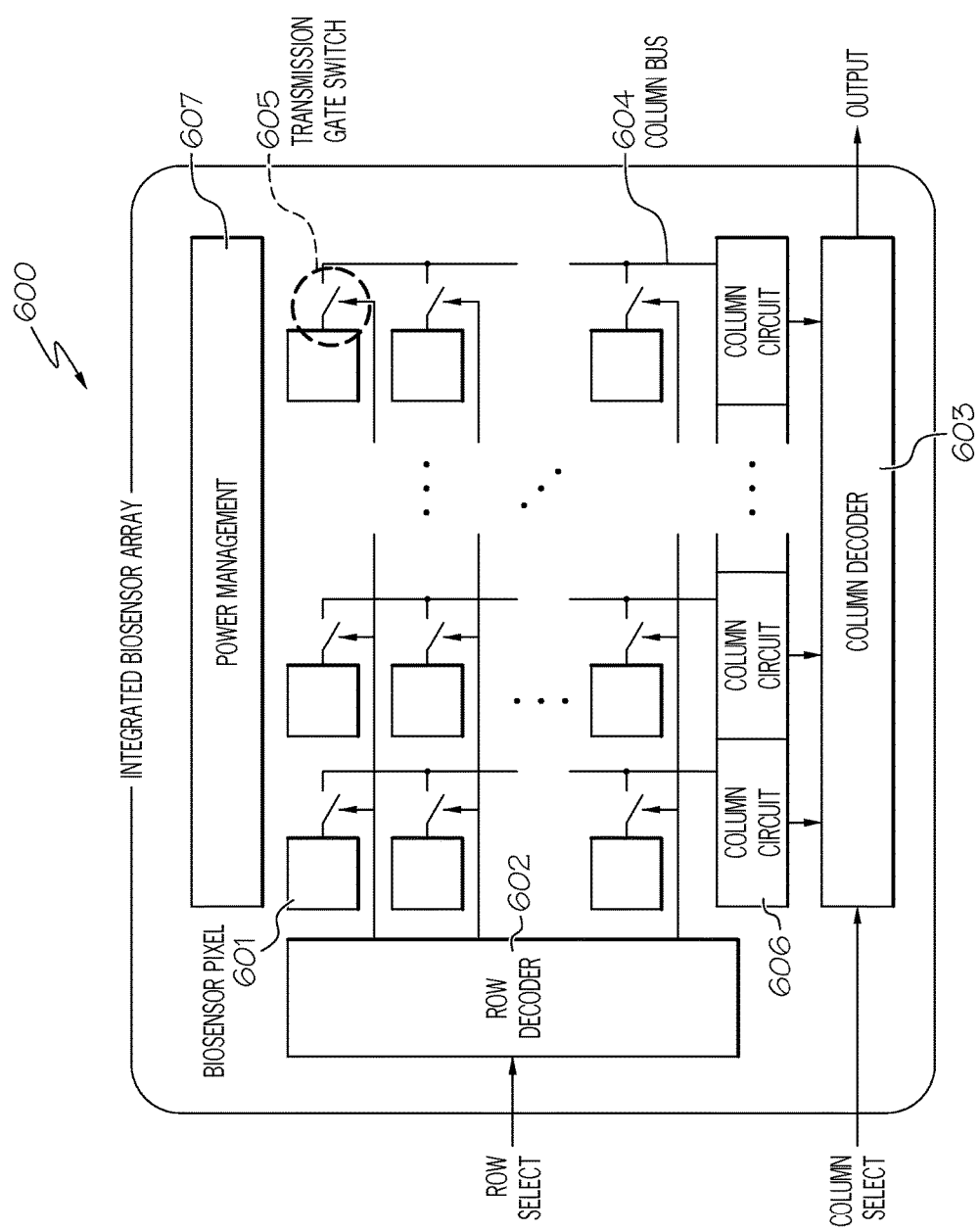
FIG. 6 illustrates an integrated biosensor array architecture in accordance with an embodiment of the present invention.

FIG. 6 illustrates an integrated electro-analytical biosensor array architecture 600 in accordance with an embodiment of the present invention. Pixels 601 are assembled in rows and columns within array 600. Individual pixels 601 are selected by using row and column decoders 602, 603, respectively. When a specific row within array 600 is selected by means of a row decoder 602, $D_{OUT}$ of all the pixels 601 in the selected row are connected to the shared column bus 604 by means of pass-transistors (e.g., transmission gate switches 605). This allows the outputs of the particular rows of interest to be connected to the column level circuitry 606. Hence, by changing the inputs of the row and column decoders 602, 603, the output of pixels 601 can be scanned and read sequentially.

The circuitry within column level circuitry 606 can offer multiple functionalities. In one embodiment, it connects a selected output of a selected pixel 601 to the output of the IC using a column decoder 603. In other embodiments, it can perform additional tasks, such as digital filtering, digital decimation and storage.

Array 600 can also include an on-chip power management and voltage generation circuitry 607, which ensures that all the blocks receive the required DC supply and reference voltages required to set the operation point of the devices in individual pixels 601. Array 600 can also include a clock and timing generation block to control the timing of the pulses which go through pixels 601.

Electro-Analysis Setup

Figure 7:
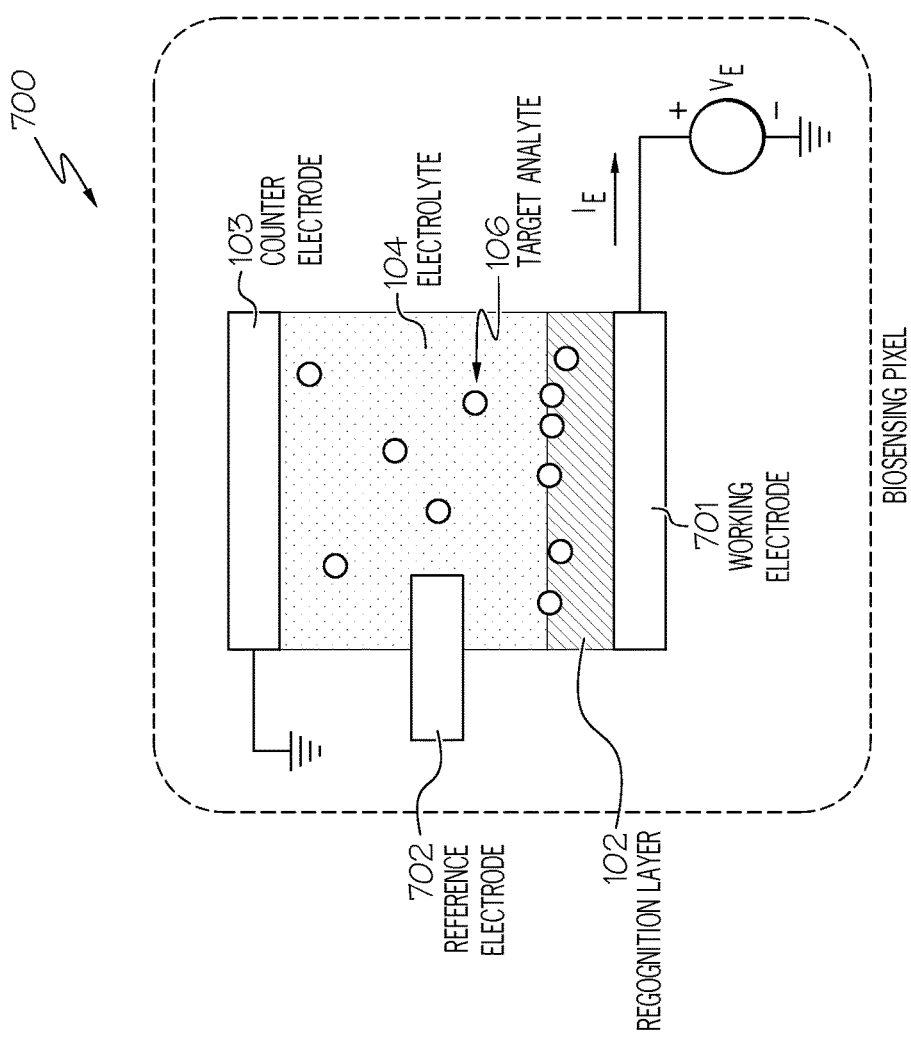
FIG. 7 illustrates a biosensing pixel containing a working electrode, a counter electrode and a reference electrode in accordance with an embodiment of the present invention.

Electro-analytical detection requires additional electrodes in the solution, besides the transducer (working) electrode of each pixel. Referring to FIG. 7, FIG. 7 illustrates a biosensing pixel 700 containing a working electrode, a counter electrode and a reference electrode in accordance with an embodiment of the present invention. The integrated electrode of each pixel 700 serves as the working electrode 701 while another electrode 103, generally referred to as the counter electrode, is also present in electrolyte 104 (or the biological buffer solution) to close the electrical circuit and allow $I_E$ to flow. Beside working and counter electrodes 701, 103, one may use a reference electrode 702 to measure the potential of electrolyte 104 at relevant coordinates within electrolyte 104 and adjust $V_E$ to compensate for unwanted spatial potential variations. It is important to note here that the use of reference electrode 702 is optional within the scope of the present invention. In one embodiment, counter electrode 103 can be created using many different methods and it can also be shared among a plurality of pixels 601 (FIG. 6) within array 600 (FIG. 6). For example, a thin wire made from non-corroding noble metals (e.g., Pt or Au) can be placed in the solution as counter electrode 103. Alternatively, counter electrodes 103 can be integrated using the metal layers of a CMOS process in similar fashion to working electrodes 701 and be placed in all pixels 601.

In one embodiment, reference electrode 702 can be created using the same methods as used in creating counter electrode 103 and may or may not be shared among pixels 601. In a specific example, large Ag/AgCl or Mg/MgCl reference electrodes 702 can be used and shared among pixels 601.

Biosensing Setup

An electro-analytical biosensor array, such as array 600 (FIG. 6), can be used in molecular detection assays, where the change in $I_E$ is measured to determine the presence or the concentration of the analyte of interest. In the present invention, integrated biosensor arrays are developed, in which capturing probe 209 (FIG. 2B) within recognition layer 102 (FIGS. 1, 4 and 7) is directly placed on top of and integrated with the integrated circuit. This permits the development of an integrated and compact detection platform, in which molecular recognition and sensing are done using the same device.

In one embodiment of the present invention, electro-analytical biosensor array 600 can be used in affinity-based detection of multiple target molecules from a single biological sample interfaced with and/or encapsulated on top of the biosensor array.

In an alternative embodiment of the present invention, electro-analytical biosensor array 600 can be used in affinity-based detection of multiple target molecules 106 (FIGS. 1 and 4) in a sample that is flowing through the surface of biosensor array 600.

Example Embodiment

Figure 8:
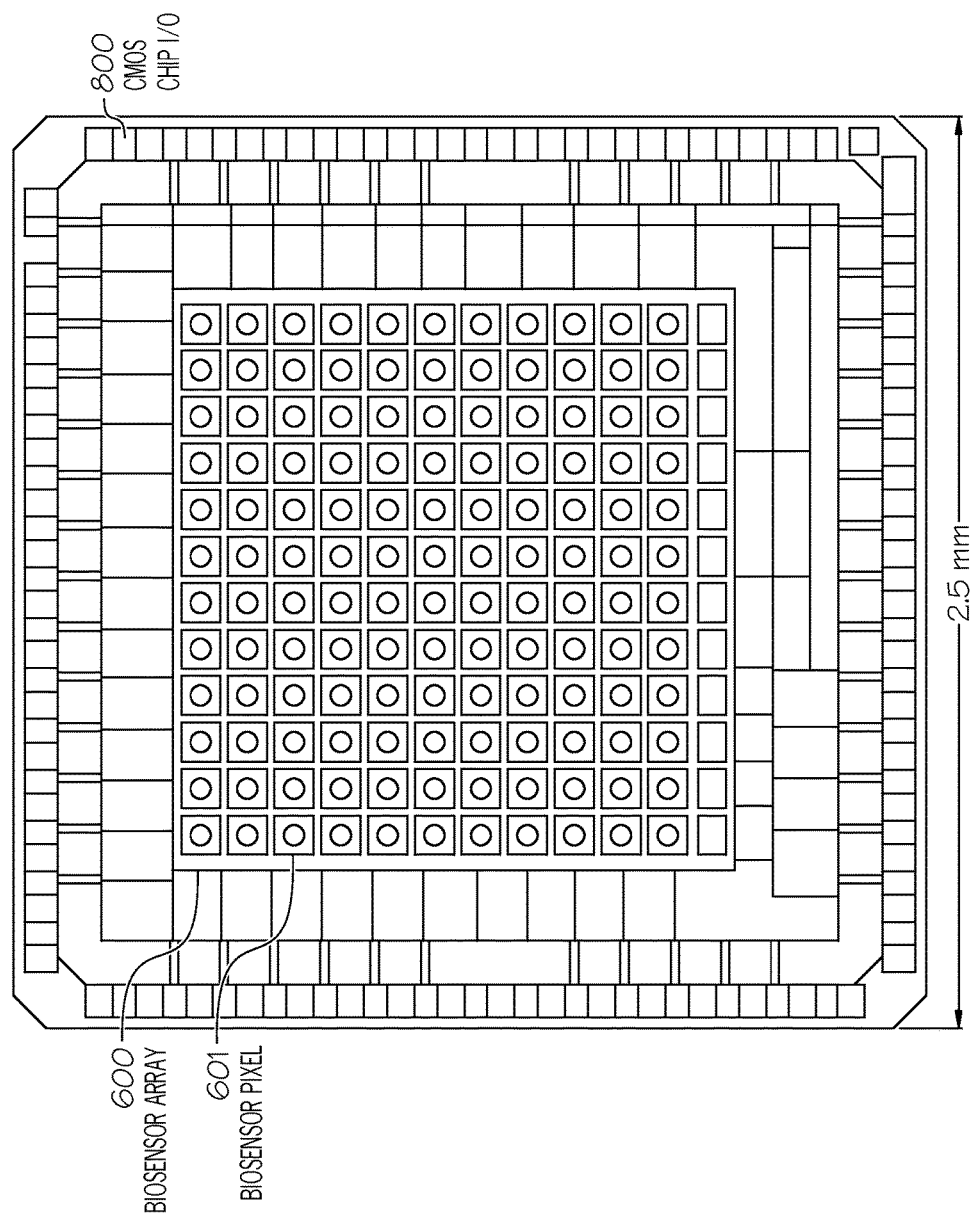
FIG. 8 is a micrograph of an implemented electro-analytical biosensor array fabricated using a 0.18 µm CMOS process in accordance with an embodiment of the present invention.

As an example embodiment, a fully-integrated electro-analytical biosensor array was fabricated using a Taiwan Semiconductor Manufacturing Company (TSMC) 0.18 µm mixed-signal CMOS process that contains 6 metal layers for interconnects on top of its silicon substrate. FIG. 8 illustrates the micrograph of this 2.5 mm×2.5 mm IC 800 in accordance with an embodiment of the present invention. Referring to FIG. 8, chip 800 includes a 12×12 array 600 of biosensing pixels 601, where each pixel 601 occupies a 120 µm×120 µm area as shown in FIG. 8.

Figure 9:
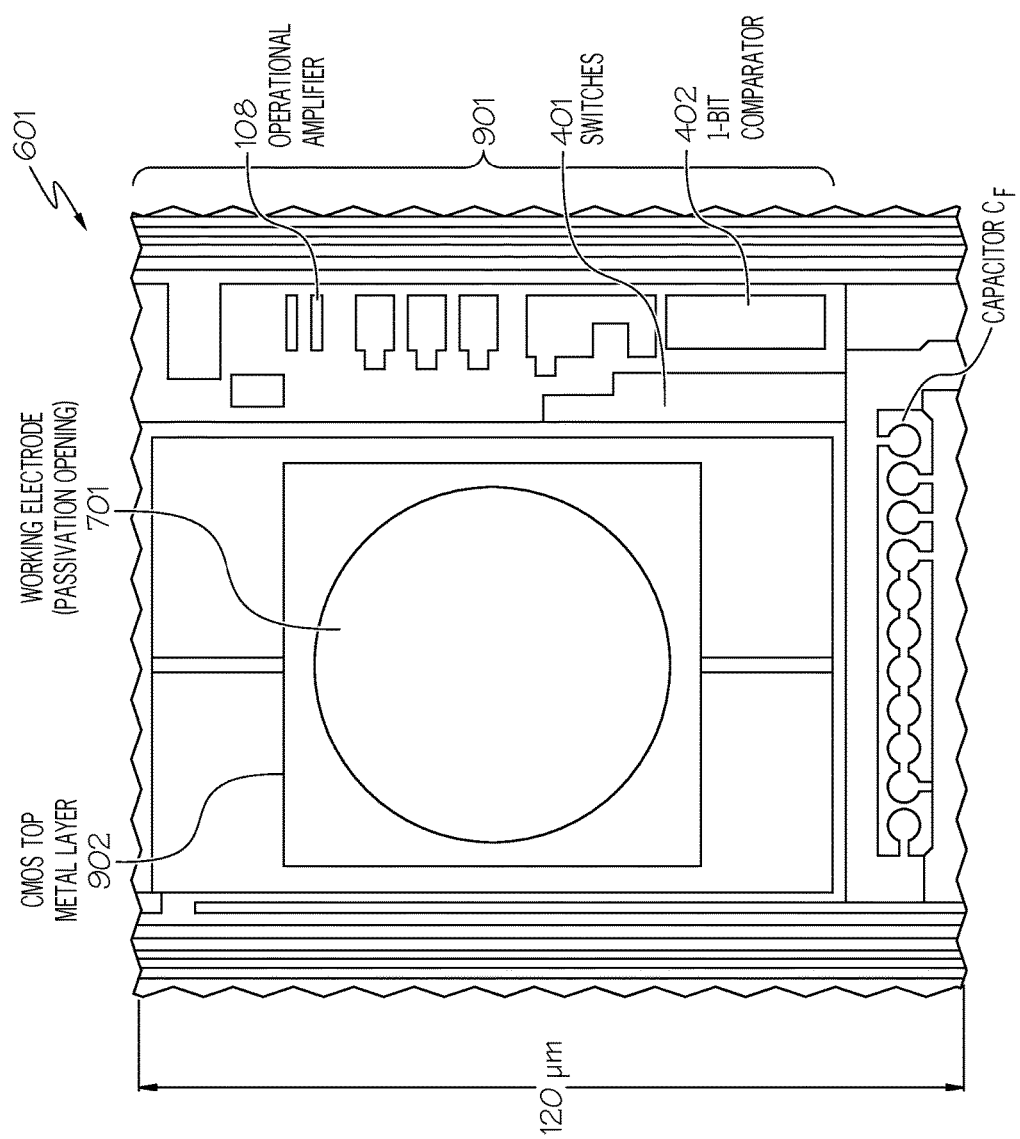
FIG. 9 is a micrograph of an individual biosensor pixel in accordance with an embodiment of the present invention.

Referring to FIG. 9, FIG. 9 is a micrograph of an individual biosensor pixel 601 in accordance with an embodiment of the present invention. Each pixel 601 in the chip includes a working electrode 701 and a Σ-Δ current detection system 901 including CTIA 107 (FIG. 4), which includes operational amplifier 108 and capacitor $C_F$, voltage comparator 402 (FIG. 4) and the switches of 1-bit DAC 401 (FIG. 4). The reference and counter electrodes 702, 103 (FIG. 7) (not shown in FIG. 9) in this system are shared among all pixels 601 and reside in the reaction chamber containing the analyses on the top pixel array, making the chip usable for electro-analysis. Furthermore, as illustrated in FIG. 9, each pixel 601 includes a top metal layer 902 surrounding working electrode 701.

Figure 10:
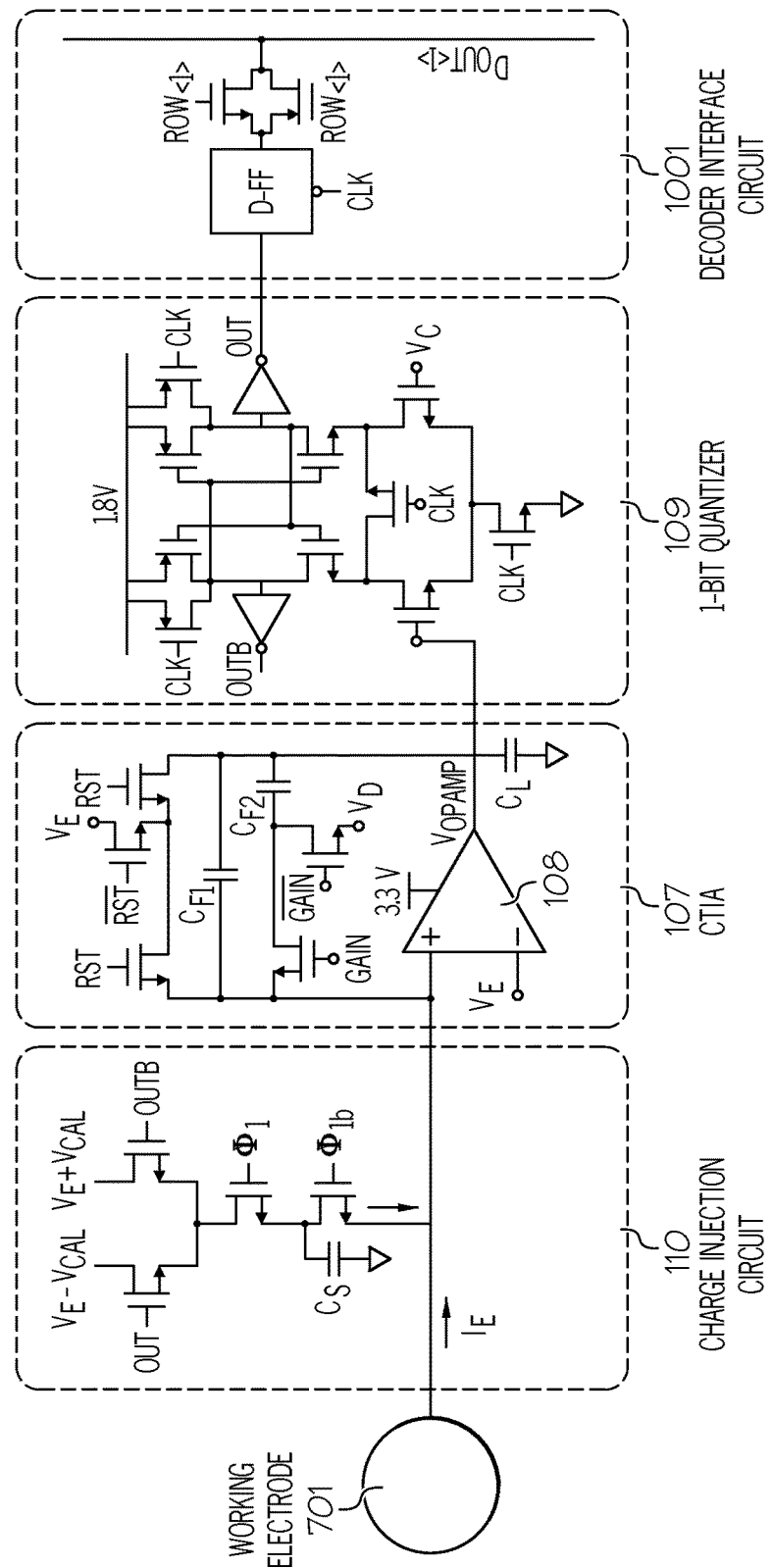
FIG. 10 illustrates the transistor-level schematic of the detection circuitry within each biosensor pixel in accordance with an embodiment of the present invention.

FIG. 10 illustrates the transistor-level schematic of the detection circuitry within each biosensor pixel 601 (FIG. 6) in accordance with an embodiment of the present invention. Specifically, FIG. 10 illustrates the circuit-level schematic of the implemented electro-analytical biosensing pixels intended to measure $I_E$ that flows through working electrode 701 (FIG. 7) of each pixel 601. Referring to FIG. 10, in conjunction with FIG. 1, as shown, CTIA 107 comprises operational amplifier 108 and programmable capacitive feedback network, which can be set to have values $C_{F1}$ or $C_{F2}+C_{F2}$, based on the logical value of the GAIN signal. The 1-bit quantizer 109 is built using a CMOS clocked (dynamic) comparator with OUT and OUTB differential outputs that control, through direct feedback, the value of the injected charge using the switch network of charge injection block 110. The digital output of this pixel 601 (such as pixel 100) is connected to the shared column bus using the in-pixel decoder circuitry 1001.

Figure 11A:
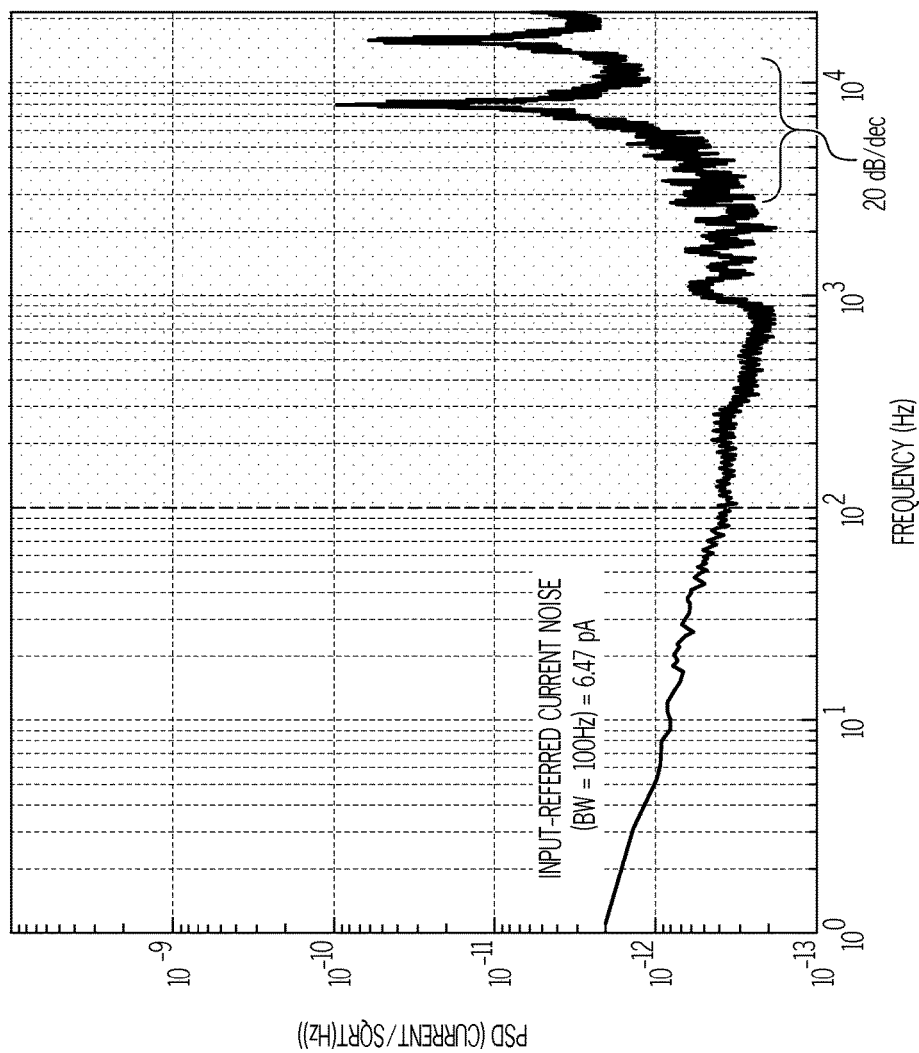
FIGS. 11A-11C illustrate the measured noise power spectral density of the implemented system for different ΣΔ oversampling rates in accordance with an embodiment of the present invention.
Figure 11B:
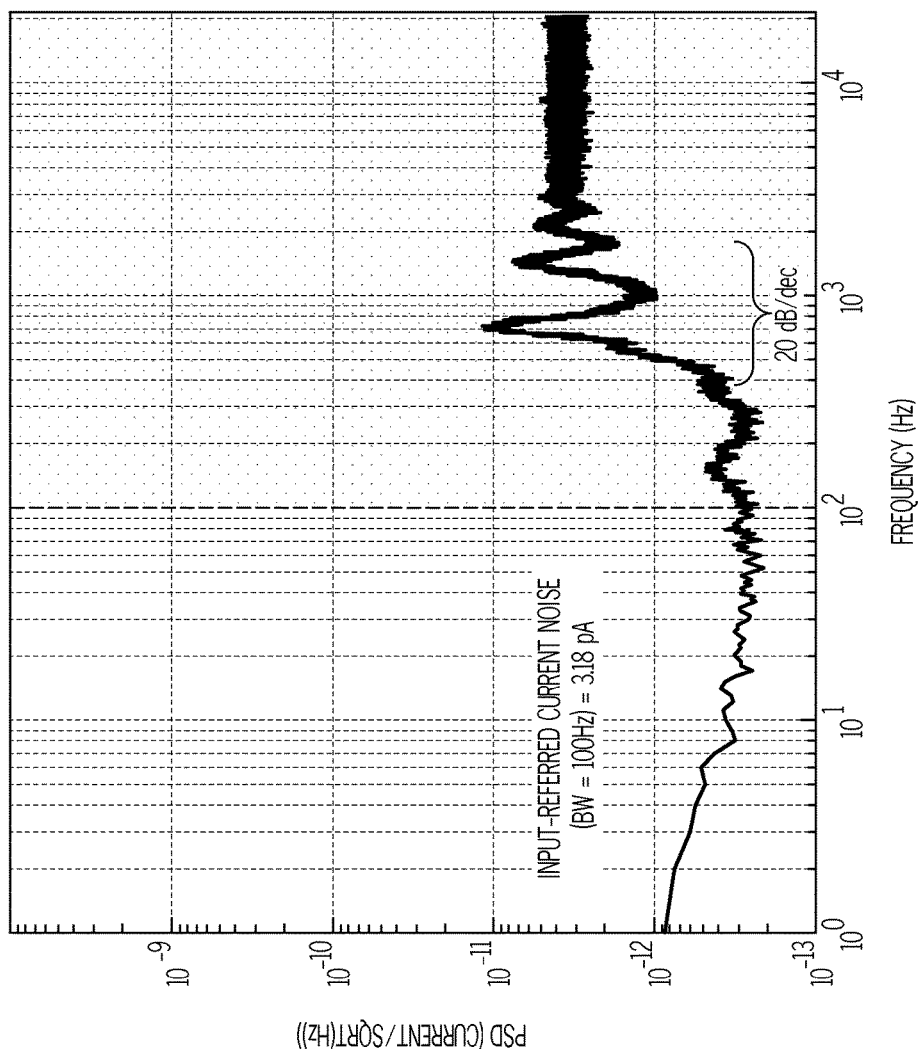
Figure 11C:
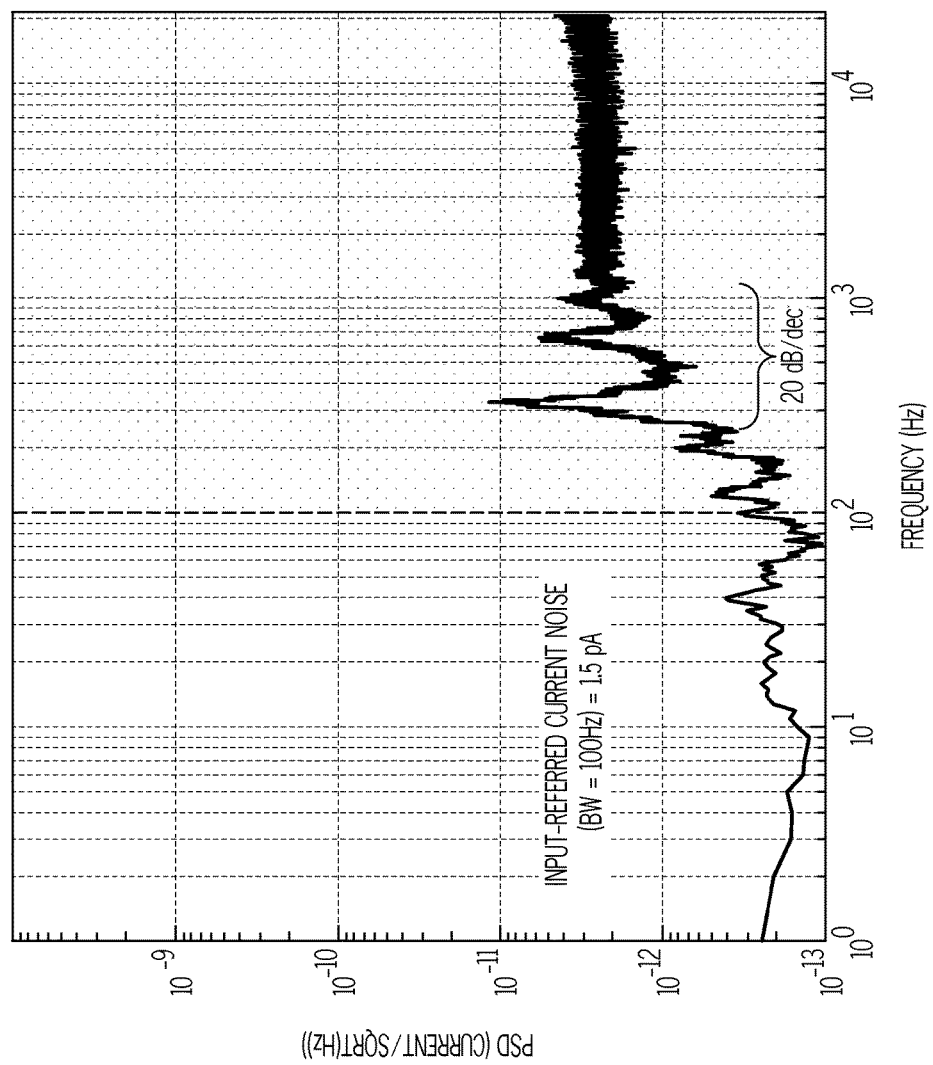

FIGS. 11A-11C illustrate the measured noise power spectral density of the implemented system for different ΣΔ oversampling rates (FIG. 11A corresponds to the oversampling rate of $1/T_s$ equal to 1 MHz, FIG. 11B corresponds to the oversampling rate of $1/T_s$ equal to 500 kHz and FIG. 11C corresponds to the oversampling rate of $1/T_s$ equal to 100 kHz) in accordance with an embodiment of the present invention. As evident in all cases, $1^{st}$-order noise shaping occurs, but depending on the oversampling rate, the useful bandwidth of the system decreases as $1/T_s$ decreases. However, for a fixed detection bandwidth of DC to 100 Hz, which was the specification for this implemented system, the noise performance of the system improves as $1/T_s$ decreases and reaches the 1.5 pA r.m.s input-referred noise at $1/T_s=100$ kHz.

Figure 12:
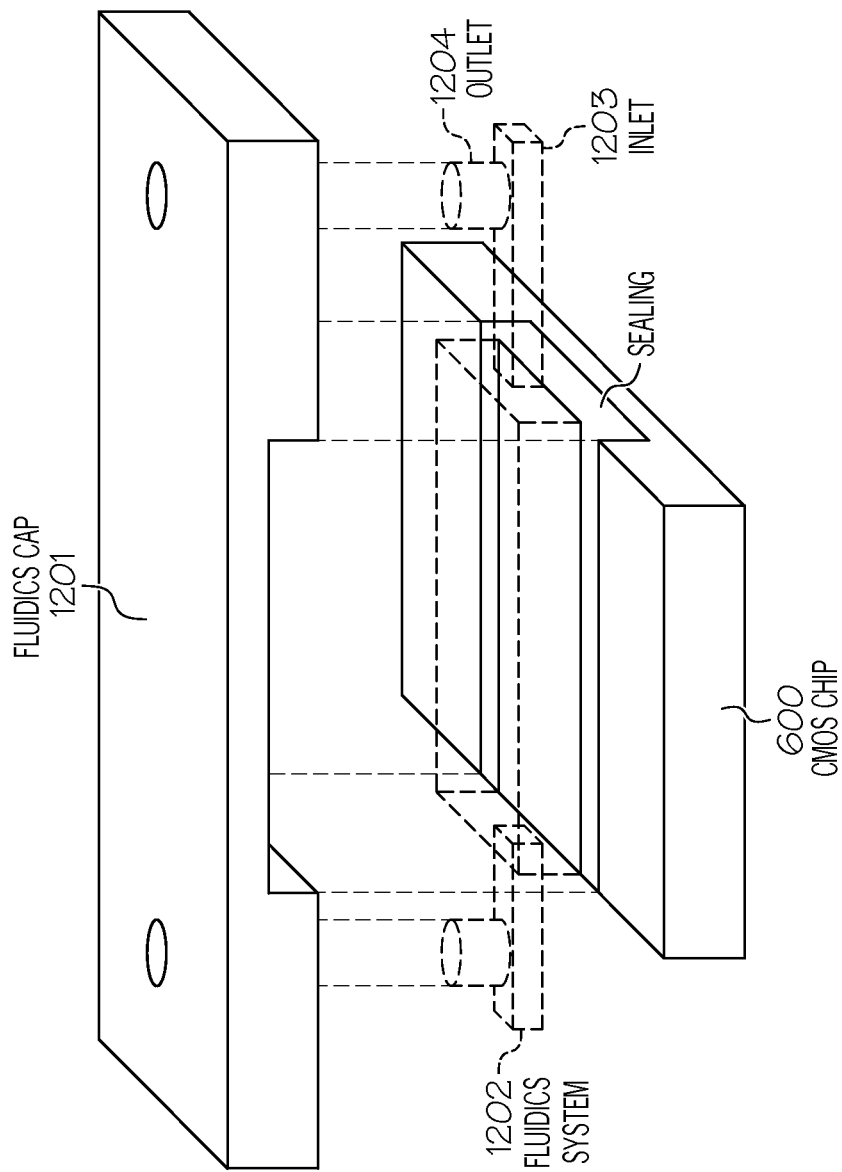
FIG. 12 illustrates the detailed structure of the fluidic cap which is placed on the implanted biosensor array to allow the insertion and extraction of biological samples in accordance with an embodiment of the present invention.

FIG. 12 illustrates a fluidic cap 1201 which is placed on the implanted biosensor array 600 to allow the insertion and extraction of biological samples in accordance with an embodiment of the present invention. In one embodiment, the function of fluidic cap 1201 is to enable a flow through a fluidic system 1202 to introduce the sample of biosensor array 600 (FIG. 6), and if necessary, extract it through an inlet 1203 and outlet 1204 while allowing electrical access to the chip 600 through wire-bonds connected to the CMOS IC pads at its periphery. In one embodiment, the volume for the reaction chamber within this cap is approximately 100 µl.

Figure 13:
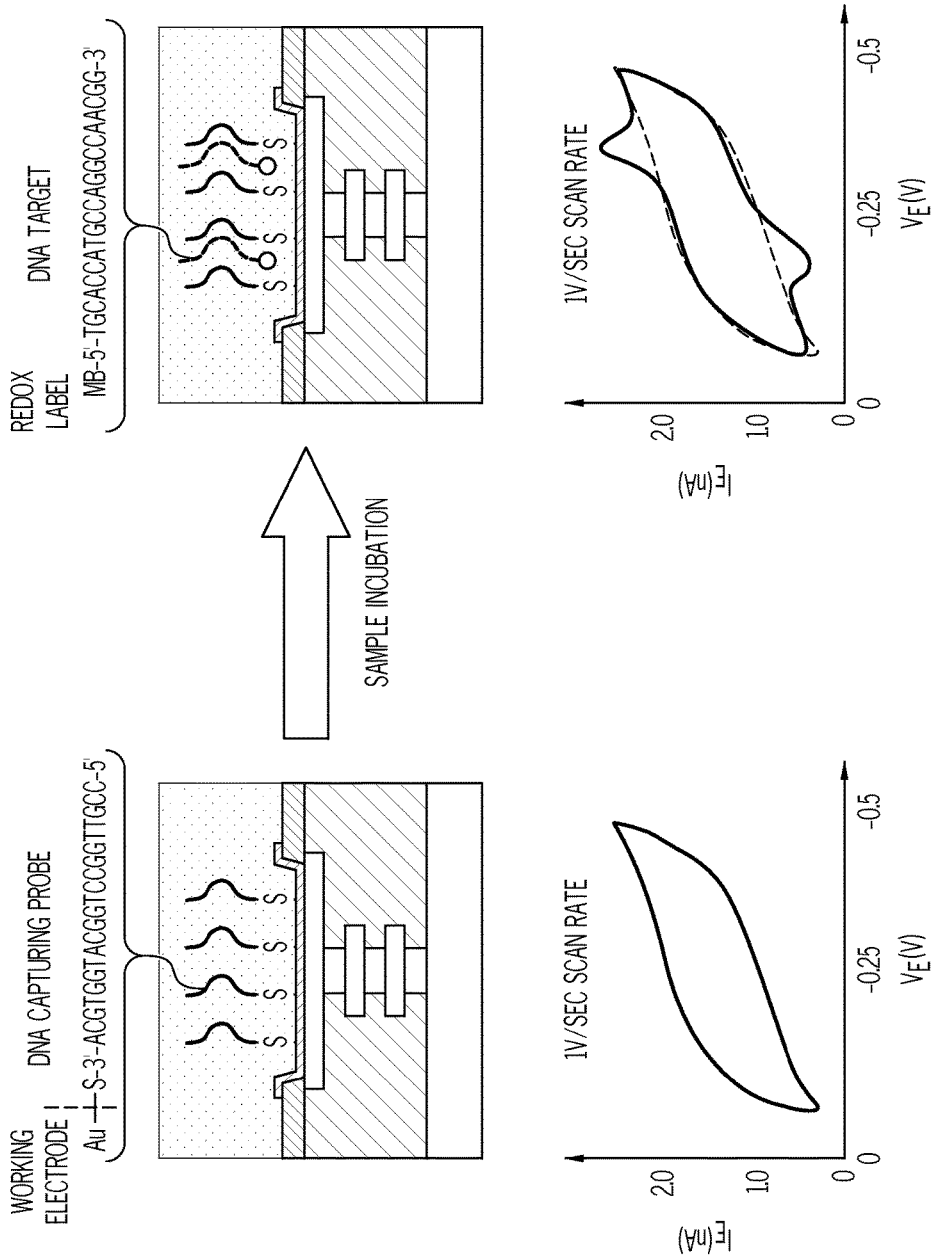
FIG. 13 illustrates a typical measured cyclic voltammetry waveform from an individual pixel when redox-based DNA detection is performed in accordance with an embodiment of the present invention.

FIG. 13 illustrates a typical measured cyclic voltammetry waveform from an individual pixel when redox-based DNA detection is performed in accordance with an embodiment of the present invention. In particular, FIG. 13 illustrates a typical example of how the system can detect specific DNA strands (as target analytes) in accordance with embodiments of the present invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A biosensor pixel, comprising:
an electrode transducer with a recognition layer, wherein said electrode transducer is configured to measure a current generated by electrochemical interactions between an analyte and said recognition layer;
a trans-impedance amplifier connected to said electrode transducer, wherein said trans-impedance amplifier is configured to convert said current into a voltage signal in real-time as said electrochemical interactions occur;
a controlled voltage source coupled to a positive input of said trans-impedance amplifier to set a potential of said electrode transducer to a value of said controlled voltage source;
a 1-bit comparator coupled to said trans-impedance amplifier; and
a 1-bit digital-to-analog converter coupled to said 1-bit comparator, wherein said 1-bit digital-to-analog converter comprises a charge injection circuit, wherein said charge injection circuit injects different levels of charge into an input of said trans-impedance amplifier at each cycle based on an output of said 1-bit comparator.

2. The biosensor pixel as recited in claim 1, wherein said recognition layer comprises capture probes.

3. The biosensor pixel as recited in claim 2, wherein said capture probes comprise nucleic acid strands.

4. The biosensor pixel as recited in claim 1, wherein said analyte comprises electro-active labels.

5. The biosensor pixel as recited in claim 4, wherein said labels comprise reduction-oxidation (redox) molecules.

6. The biosensor pixel as recited in claim 1, wherein a white noise source is inputted to said 1-bit comparator.

7. The biosensor pixel as recited in claim 1, wherein said injected charge is a controlled amplitude and adjustable current.

8. The biosensor pixel as recited in claim 1, wherein said injected charge is added to or subtracted from said input of said trans-impedance amplifier.

9. The biosensor pixel as recited in claim 1, wherein said injected charge is a background signal, wherein said background signal is a signal independent from said measured current generated by electrochemical interactions between said analyte and said recognition layer.

10. A planar two-dimensional biosensor array architecture, comprising:
a plurality of biosensor pixels assembled in rows and columns, wherein each of said plurality of biosensor pixels comprises:
an inert electrode transducer configured to sense a current generated by electrochemical interactions occurring at individual recognition layer regions of every pixel in response to different electrical voltages being placed across an electrode transducer-electrolyte interface for that pixel;
a trans-impedance amplifier connected to said electrode transducer, wherein said trans-impedance amplifier is configured to convert said current into a voltage signal in real-time as said electrochemical interactions occur;
a controlled voltage source coupled to a positive input of said trans-impedance amplifier;
a 1-bit comparator coupled to said trans-impedance amplifier; and
a 1-bit digital-to-analog converter coupled to said 1-bit comparator, wherein said 1-bit digital-to-analog converter comprises a charge injection circuit, wherein said charge injection circuit injects different levels of charge into an input of said trans-impedance amplifier at each cycle based on an output of said 1-bit comparator; and
row and column decoders coupled to said plurality of biosensor pixels, wherein said row and column decoders are configured to select individual pixels of said plurality of biosensor pixels and access them one at a time.

11. The biosensor array architecture as recited in claim 10 further comprises: a power management circuit configured to ensure that each of said plurality of biosensor pixels receives an appropriate supply and reference voltage.

12. The biosensor array architecture as recited in claim 10, wherein a recognition layer of a biosensor pixel of said plurality of biosensor pixels comprises capture probes.

13. The biosensor array architecture as recited in claim 12, wherein said capture probes comprise nucleic acid strands.

14. The biosensor array architecture as recited in claim 10, wherein said inert electrode transducer is configured to sense said current generated by said electrochemical interactions between an analyte and a recognition layer of a biosensor pixel of said plurality of biosensor pixels, wherein said analyte comprises electro-active labels.

15. The biosensor array architecture as recited in claim 14, wherein said labels comprise reduction-oxidation (redox) molecules.

16. The biosensor array architecture as recited in claim 10, wherein said injected charge is a controlled amplitude and adjustable current.

17. The biosensor array architecture as recited in claim 10, wherein said injected charge is added to or subtracted from said input of said trans-impedance amplifier.

* * * * *